United States Patent
Damm et al.

(10) Patent No.: US 9,158,007 B2
(45) Date of Patent: Oct. 13, 2015

(54) SCINTILLATION DETECTOR

(71) Applicant: Endress + Hauser GmbH + Co. KG, Maulburg (DE)

(72) Inventors: Hartmut Damm, Teningen (DE); Simon Weidenbruch, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 0 days.

(21) Appl. No.: 14/375,218

(22) PCT Filed: Dec. 17, 2012

(86) PCT No.: PCT/EP2012/075784
§ 371 (c)(1),
(2) Date: Jul. 29, 2014

(87) PCT Pub. No.: WO2013/113447
PCT Pub. Date: Aug. 8, 2013

(65) Prior Publication Data
US 2015/0014547 A1      Jan. 15, 2015

(30) Foreign Application Priority Data
Jan. 31, 2012 (DE) .......................... 10 2012 100 768

(51) Int. Cl.
*G01T 1/20* (2006.01)
*G01F 23/288* (2006.01)
*G01N 9/24* (2006.01)

(52) U.S. Cl.
CPC ............ *G01T 1/2006* (2013.01); *G01F 23/288* (2013.01); *G01N 9/24* (2013.01); *G01T 1/20* (2013.01); *G01T 1/2002* (2013.01)

(58) Field of Classification Search
CPC ................................. G01T 1/20; G01F 23/288
USPC ........................... 250/361 R, 367–369, 357.1
See application file for complete search history.

(56) References Cited

U.S. PATENT DOCUMENTS 3,717,760 A    2/1973  Martin
5,629,515 A    5/1997  Maekawa
(Continued)

FOREIGN PATENT DOCUMENTS

DE    20103881 U1    7/2001
EP    1912045 A1     4/2008
EP    2354809 A2     8/2011

OTHER PUBLICATIONS

German Search Report, DPMA, Munich, Oct. 23, 2012.
(Continued)

*Primary Examiner* — David Porta
*Assistant Examiner* — Meenakshi Sahu
(74) *Attorney, Agent, or Firm* — Bacon & Thomas, PLLC

(57) ABSTRACT

A scintillation detector, especially one for a radiometric measuring device for measuring and/or monitoring a measured variable, especially a fill level of a fill substance located in a container, for covering a predeterminable measuring range as flexibly as possible in shape and length. To this end, the scintillation detector comprises two or more scintillators arranged in series relative to one another for converting thereon falling, radioactive radiation into light flashes, whose light propagates in the respective scintillator toward its ends. Arranged between the scintillators are optical coupling elements, which establish light transmitting connections between adjoining pairs of scintillators. Connected at an end of the series is a photoelectric transducer, which converts light occurring in the series into an electrical signal corresponding to a radiation intensity striking the scintillators. According to the invention, at least one of the coupling elements is a mechanically flexible element, which includes a bundle of light conducting fibers, via which transmission of the light between the two scintillators connected with one another via the fibers occurs.

10 Claims, 2 Drawing Sheets

(56) References Cited

U.S. PATENT DOCUMENTS

| | | |
|---|---|---|
| 5,675,151 A | 10/1997 | Oka |
| 5,780,856 A * | 7/1998 | Oka et al. ............... 250/367 |
| 6,563,120 B1 | 5/2003 | Baldwin |
| 7,629,584 B2 | 12/2009 | Murmann |
| 8,426,827 B2 | 4/2013 | Cahill |
| 2002/0117625 A1 * | 8/2002 | Pandelisev ............ 250/368 |
| 2003/0091820 A1 * | 5/2003 | Robbins ................ 428/373 |
| 2003/0098418 A1 | 5/2003 | Joubert |
| 2004/0025569 A1 * | 2/2004 | Damm et al. ............ 73/32 R |
| 2009/0026375 A1 | 1/2009 | Doshi |
| 2009/0041404 A1 * | 2/2009 | Stoddart ................ 385/12 |
| 2011/0260067 A1 | 10/2011 | Tamda et al. |

OTHER PUBLICATIONS

International Search Report, EPO, The Netherlands, May 31, 2013.
English Translation of the International Preliminary Report on Patentability, WIPO, Geneva, Switzerland, Aug. 14, 2014.

* cited by examiner

SCINTILLATION DETECTOR

TECHNICAL FIELD

The invention relates to a scintillation detector, especially to a radiometric measuring device, for measuring and/or monitoring a measured variable, especially a fill level or a density of a fill substance located in a container, comprising two or more scintillators arranged in series relative to one another for converting thereon falling, radioactive radiation into light flashes, whose light propagates in the respective scintillator toward its ends, optical coupling elements arranged between adjoining scintillators for establishing light transmitting connections between adjoining scintillators, and, connected at an end of the series, a photoelectric transducer, which converts light striking the series into an electrical signal corresponding to a radiation intensity striking the scintillators.

BACKGROUND DISCUSSION

Radiometric measuring devices are usually applied when conventional measuring devices cannot be used due to especially rough conditions at the measuring location. Existing very frequently at the measuring location are e.g. extremely high temperatures and pressures or chemically and/or mechanically very aggressive environmental influences, which make the use of other measuring methods impossible.

Such devices typically include a radioactive radiator, which during operation sends radioactive radiation through the container, and, arranged on a side of the container lying opposite the radiator, a detector, which serves to receive a measured variable dependent, radiation intensity penetrating through the container and to convert such into an electrical signal.

In radiometric measurements technology, a radioactive radiator, e.g. a Co60 or Cs137 preparation, is placed in a radiation protection container at a measuring location, e.g. a container containing a fill substance. The container containing the fill substance can be e.g. a tank, a vat, a pipe or tube, a conveyor belt or any other form of containment.

The radiation protection container has a window, through which radiation emitted from the radiator positioned at a measuring location leaves the radiation protection container for the fill substance container.

Usually, the window is sized to provide a radiation direction such that the radiation penetrates that region of the container that needs to be registered for the measuring. On the oppositely lying side of the fill substance container, the emerging radiation intensity, changed by the fill substance at its fill level, respectively by a change in the density of the fill substance, is registered quantitatively with a detector. The emerging radiation intensity depends on the geometric arrangement and on the absorption. The latter in the case of fill level measurement is dependent on the amount and density of the fill substance in the container located in the path of the radiation. As a result, the emerging radiation intensity is a measure for the current fill level, respectively the current density, of the fill substance in the container.

Currently usually applied as a detector are scintillation detectors having a solid, rigid, scintillation rod, at whose one end a photoelectric transducer, e.g. a photomultiplier, is arranged. The scintillation rod is composed of a special synthetic material, such as e.g. polystyrene (PS) or polyvinyl toluene (PVT), which is optically very pure. Gamma radiation leads to the occurrence of light flashes in the scintillation material. The light of these light flashes is registered by the photomultiplier and converted into electrical pulses. Connected to the photomultiplier is a measuring device electronics, which, based on the electrical pulses, determines a pulse rate, with which the pulses occur. The pulse rate depends on the radiation intensity arriving at the photoelectric transducer and, thus, is a measure for the measured variable to be determined.

Scintillation rods are obtainable today in lengths of about 0.4 m up to 2 m. If a length of 2 m is not sufficient to cover the region to be measured, radiometric measuring devices comprising two or more detectors can be provided, each of which covers a portion of the region to be measured.

An example of this is presented in German Patent DE 10 2004 007 680 A1. The radiometric measuring device described there provides that detector is equipped with a scintillation rod and a photomultiplier connected terminally thereto. Each detector produces a pulse rate corresponding to the radiation intensity striking thereon, and, based on the pulse rates of the individual detectors, a sum signal is derived, which corresponds to the total radiation intensity striking the detectors over the measuring range metrologically registered by the detectors.

This solution has the advantage that the individual detectors can be flexibly arranged and, thus, can be matched to the spatial conditions at the location of use, especially to the container geometry. Disadvantageous, however, is that each detector requires its own photoelectric transducer.

An alternative solution is known from German Gebrauchsmuster (utility model) DE 201 03 881 U1. Such describes a scintillation detector for a radiometric measuring device for measuring a fill level of a fill substance located in a container, comprising:

two or more scintillators arranged in a series relative to one another for converting thereon falling, radioactive radiation into light flashes, whose light propagates in the respective scintillator toward its ends;

optical coupling elements arranged between the scintillators for establishing light transmitting connections between adjoining pairs of scintillators; and, connected to an end of the series, a photoelectric transducer, which converts light occurring in the series into an electrical signal corresponding to a radiation intensity striking the scintillators.

The scintillators are placed in a protective tube constructed of segments.

In a first variant described in the above-noted DE 201 03 881 U1, the scintillators are straight rods, which are arranged end to end in a straight line with interpositioning of a material effecting optical coupling, especially a material in the form of silicone disks or silicone oil. In such case, there arises the problem that the different thermal expansions of the scintillators and the segments of the protective tube must be absorbed, respectively cancelled, in order to prevent a degrading of the optical coupling between the aligned scintillators. This is effected in the described variant by a spring, which presses the scintillators toward one another and the straight rod composed of the scintillators, as a whole, toward the photoelectric transducer.

Additionally, a second variant is described, in the case of which there is constructed from the individual scintillators a sectionally angled, total scintillator. For this, wedge shaped, intermediate pieces are inserted between individual scintillators. Described examples of the intermediate pieces are a wedge shaped silicone disk and a wedge shaped light conductor. In such case, the end faces of the light conductors are optically coupled via silicone oil to the end faces of the adjoining scintillators.

Also here, there arises naturally the problem of the different thermal expansions of the scintillators and the segments of the protective tube, a problem that, in spite of the sectionally angled shape, must be solved, in order to assure the optical coupling, especially when silicone oil is being used.

Moreover, there arises here the problem that, at the wedge shaped intermediate pieces, due to the basically straight line light propagation, a certain part of the light to be transmitted to the adjoining scintillators escapes to the exterior. A part of this light escape arises due to the directional change directly outside the intermediate piece. A further part is lost, because, after the directional change through the intermediate piece, the outer surfaces of the following scintillator are no longer at the angle for total reflection, and, thus, light escapes to the exterior from the following scintillator. The lost light is greater, the more strongly the angling caused by the particular intermediate pieces. This lost light does not get to the photoelectric transducer and, thus, is not registered. Light losses act directly disadvantageously on the measuring sensitivity of the measuring device. An as high as possible light efficiency is, however, exactly especially important for these detectors, in the case of which light travels a greater path length through a number of individual scintillators arranged in series. Accordingly, here, both the angle sizes and also the number of the angles are limited. Correspondingly, also the options for matching the spatial conditions at the location of use, for instance round container shapes, are greatly limited.

SUMMARY OF THE INVENTION

An object of the invention is to provide a scintillation detector, with which a predeterminable measuring range can be covered as flexibly as possible as regards both shape and length.

To this end, the invention resides in a scintillation detector, especially one for a radiometric measuring device, for measuring and/or monitoring a measured variable, especially a fill level or a density, of a fill substance located in a container, comprising:
  two or more scintillators arranged in series relative to one another for converting thereon falling, radioactive radiation into light flashes, whose light propagates in the respective scintillator toward its ends:
  optical coupling elements arranged between adjoining scintillators for establishing light transmitting connections between adjoining scintillators: and
  connected at an end of the series, a photoelectric transducer, which converts light occurring in the series into an electrical signal corresponding to a radiation intensity striking the scintillators, wherein,
according to the invention, at least one of the coupling elements is a mechanically flexible element, which includes a bundle of light conducting fibers, via which transmission of light between the two scintillators connected with one another via the fibers occurs.

In a preferred embodiment, the fibers are light conducting, scintillation fibers.

Alternatively, the fibers can also be glass fibers or plastic light conductors.

In a further development, each of two ends of the bundle is held in a collar, which is mechanically connectable via a centering sleeve with an end of the scintillator to be connected thereto.

In a still further development,
  the fibers of the bundle are terminally planarly polished, and
  each of the polished ends of the bundle in the assembled state lies, with interpositioning of a coupling paste, against a planarly polished end face of a respectively adjoining scintillator.

In an additional further development,
  a modularly constructed protective tube is provided for accommodating the scintillators, and
  the protective tube is composed of segments, whose internal spaces are matched to the spatial dimensions of the scintillators and the coupling elements to be accommodated.

In a still further development, segments provided for accommodating the flexible coupling elements are embodied as flexible bellows.

In a preferred embodiment, the segment of the protective tube provided on the end facing away from the photoelectric transducer is embodied as a cap, which seals an inner space of the protective tube.

In an additional further development, the fibers of the coupling elements have a slight excess length, which is greater than or equal to a maximal, thermal expansion related, separation change between the scintillators connected with one another by the respective coupling element.

Another further development provides that
  the scintillators are arranged in an inner space of a protective tube, whose photoelectric transducer facing end is terminated by means of a light transmissive, especially glass, plug,
  the photoelectric transducer is arranged in a separate housing,
  the housing is connectable mechanically with the protective tube via a releasable mechanical connection, and
  the housing has a light transmissive, especially glass, plug, via which the photoelectric transducer is optically connectable to the series of scintillators.

BRIEF DESCRIPTION OF THE DRAWINGS

The invention and other advantages will now be explained in greater detail based on the figures of the drawing, in which an example of an embodiment is presented; equal parts are provided in the figures with equal reference characters. The figures of the drawing show as follows.

DETAILED DISCUSSION IN CONJUNCTION WITH THE DRAWINGS

Figure 1:
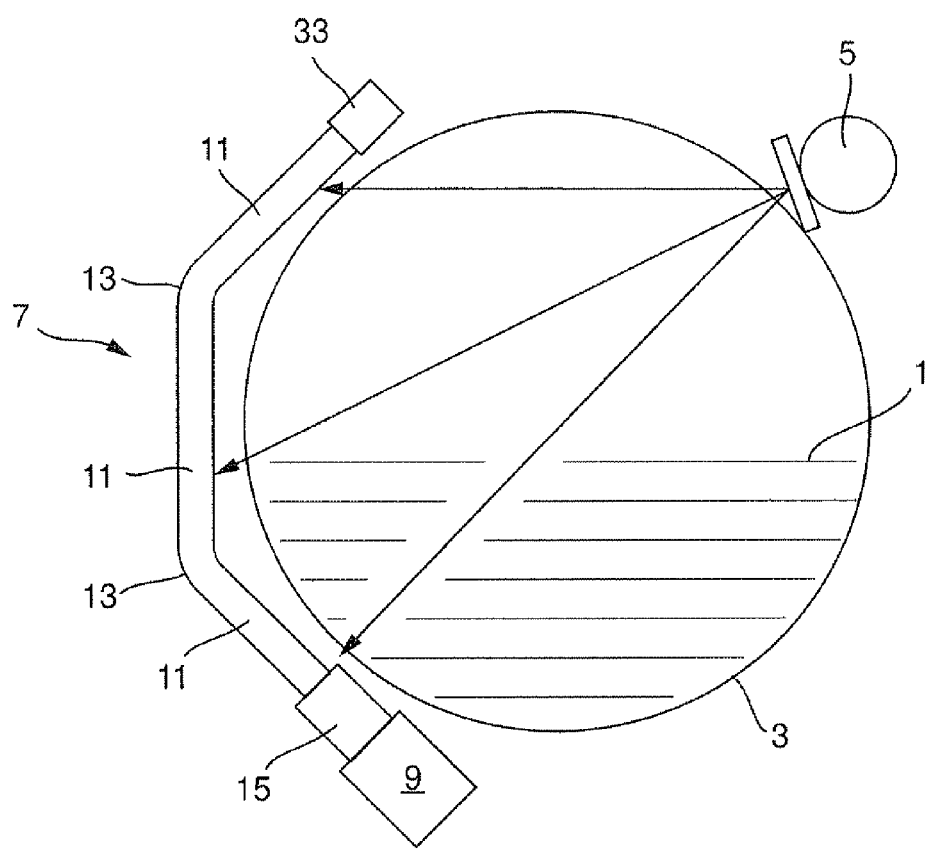
FIG. 1 is a fill level measuring arrangement.

The invention relates to a scintillation detector for a radiometric measuring device for measuring and/or monitoring a measured variable. The scintillation detector is especially applicable in radiometric fill-level measuring devices. FIG. 1 shows an example of an embodiment of a fill level measuring arrangement having such a fill-level measuring device.

Without prejudice to the selected application example of fill level measurement, the scintillation detector of the invention can naturally also be applied as a detector for fill-level monitoring, in a radiometric density measuring device, or in other measuring devices, in the case of which a measuring of a radiation intensity is required, which strikes, as a whole, in a region to be registered for measurement purposes.

The measuring arrangement includes a container 3 fillable with a fill substance 1 and, mounted externally at the container 3, a radioactive radiator 5, which, in measurement operation, sends radioactive radiation through the container 3. Radiator 5 includes a radiation protection container, in which a radioactive preparation, e.g. a Co60 or Cs137 preparation, is placed. The radiation protection container has a window, through which the radiation escapes in a radiating direction predetermined by the orientation of the opening and irradiates the container 3. Arranged on a side of the container 3 lying opposite the radiator 5 is a scintillation detector 7 of the invention. Scintillation detector 7 serves to receive radiation intensity penetrating through the container 3 as a function of the measured variable, here the fill level in the container 3, over a predetermined region to be registered application specifically for measurement by the scintillation detector 7, and to convert the received radiation into an electrical signal corresponding to the radiation intensity striking thereon. The electrical signal is then forwarded to a measuring electronics 9 of the radiometric measuring device connected to the scintillation detector 7 for additional evaluation and/or processing. Based on the electrical signal, the measuring electronics 9 determines the measured variable.

Scintillation detector 7 includes two or more serially arranged scintillators 11, which convert thereon falling, radioactive radiation into light flashes. The scintillators 11 are, for example, scintillation rods of a scintillating, synthetic material, such as e.g. optically very pure polystyrene (PS) or polyvinyl toluene (PVT). Gamma radiation causes light flashes in the scintillation material. The light of the light flashes propagates in the respective scintillator 11 toward its ends.

Arranged between adjoining scintillators 11 is, in each case, an optical coupling element 13, in order to effect light transmitting connections between adjoining pairs of scintillators 11.

Arranged at one end of the serially interconnected scintillators 11 is a photoelectric transducer 15, which converts light arising in the serially interconnected scintillators 11 into an electrical signal corresponding to a radiation intensity totally striking the scintillators 11. Especially suited for this is a photomultiplier, which registers light striking thereon and converts such into electrical pulses. The pulse rate of these pulses depends on the radiation intensity and, thus, is a measure for the measured variable to be determined. The photoelectric transducer 15 is connected to the measuring electronics 9, which then determines, for example, based on the pulse rate, the fill level of the fill substance 1 in the container 3.

Figure 2:
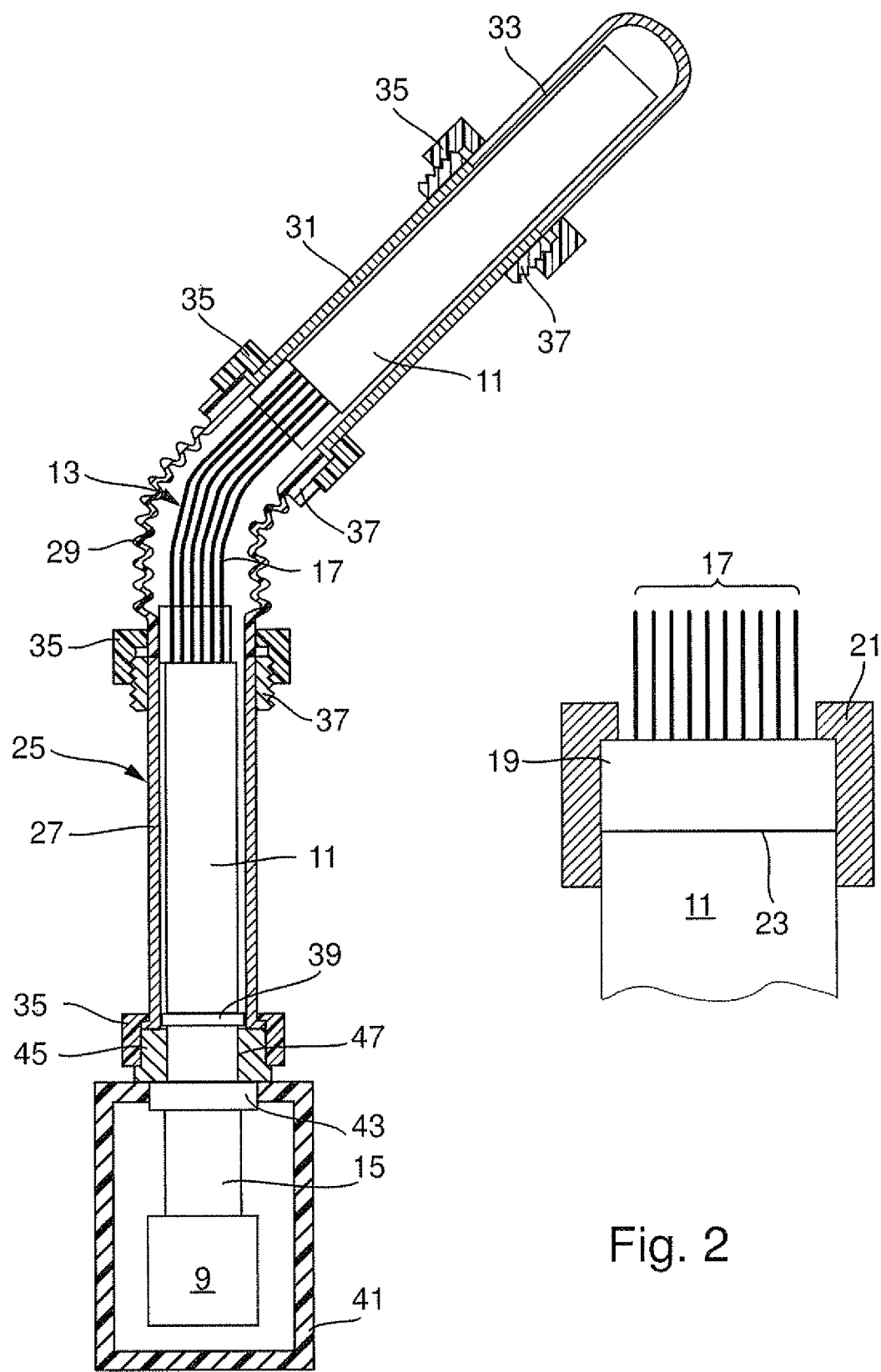
FIG. 2 is a scintillation detector of the invention.

FIG. 2 shows an example of an embodiment of a scintillation detector of the invention with two rod-shaped scintillators 11 connected with one another via an optical coupling element 13. In equal manner, naturally also scintillation detectors with three or more scintillators 11 connected with one another via coupling elements 13 can be provided.

According to the invention, the coupling element 13 is a mechanically flexible element, which includes a bundle of light conducting fibers 17, via which the transmission of the light between the two scintillators 11 connected with one another via the fibers 17 occurs.

Light conducting fibers 17 offer the advantage that they are mechanically flexible and their light transmission characteristics are largely independent of the spatial orientation of the fibers 17.

In this way, a high measure of flexibility is achieved in the joint, without that such degrades the light transmission between the individual scintillators 11 connected via coupling elements 13. In such case, the degree of bending at each joint realizable without significant light losses is greater, the smaller the fiber diameter, respectively the fiber thickness. Thus, by corresponding orientation and arrangement of the fibers 17 while maintaining the bending radius predetermined by the fiber thickness, respectively the fiber diameter, even light conduction paths extending at an angle of 90° or, in the extreme case, even 180° are implementable. By an appropriate selection of number and length of the individual scintillators 11, the scintillation detector of the invention is therewith adaptable extremely flexibly to the conditions existing at the location of use.

This offers the advantage that measuring ranges extremely flexibly predeterminable in shape and length can be covered with the scintillation detectors of the invention, without significant light losses occurring in the regions of the coupling elements 13, where the propagation direction of the transmitted light is changed.

Preferably, the fibers 17 are light conducting, scintillation fibers. Scintillation fibers represent an obtainable commodity. They transduce thereon falling, radioactive radiation into light flashes, whose light propagates toward both ends of the respective scintillation fiber. Correspondingly, the light fraction propagating in the interconnected series toward the photoelectric transducer 15 is transmitted via the particular scintillation fiber to the respectively next scintillator 11, and from there to the photoelectric transducer 15. Scintillation fibers offer here the advantage that even radioactive radiation striking the coupling elements 13 is registered for measurement.

Alternatively, the fibers 17 can be just light conductors, especially in the form of light conducting glass fibers or plastic light conductors. This usually cost effective variant is preferably applied in detectors, in which the length fraction of the coupling elements 13 to the length of the total measuring range covered by the detector is small.

Each of the two ends of the bundle is held, especially adhered, in a collar 19, which is connectable via a centering sleeve 21 with the respective end of the scintillator 11 to be connected mechanically thereto, especially by adhesive. This is shown in FIG. 2 in the enlarged detail illustration to the right of the scintillation detector.

For improving the optical coupling, both the end faces of the scintillators 11 adjoining the coupling element 13 as well as also the fibers 17 of the bundle are terminally planarly polished. Preferably, a coupling paste 23 is applied on the end faces of the scintillators 11, so that the polished ends of the bundle in the mounted state lie, with interpositioning of the coupling paste 23, against the planarly polished end faces of the ends of the scintillators 11.

Preferably, the scintillation detector includes a protective tube 25 for accommodating the serially arranged scintillators 11 and the coupling elements 13. The protective tube 25 is composed, for example, of metal, and is preferably modularly constructed. To this end, it is composed of segments 27, 29, 31, 33, whose internal spaces are matched to the spatial dimensions of the scintillators 11 and the coupling elements 13 respectively to be accommodated therein.

The individual segments 27, 29, 31, 33 are preferably releasably mechanically connectable with one another via centering sleeves 35. The happens, for example, by providing each segment 27, 29, 31, 33 with a centering sleeve 35 rotatably held on the end of the respective segment and having an internal thread, which is screwable onto an external thread 37 of the respectively next segment 27, 29, 31 to be connected mechanically therewith.

In connection with the protective tube 25 the coupling elements 13 of the invention offer the advantage that no special additional precautionary measures are needed for accommodating or equalizing the different thermal expansions of the scintillators 11 and the protective tube 25. Instead, it is sufficient that the fibers 17 have a slight excess length, which is greater than or equal to a maximal separation change arising between the respectively interconnected scintillators 11 due to the different thermal expansions as a function of temperature. Therewith, temperature dependent stressing of the mechanical connections between the coupling elements 13 and the therewith respectively connected scintillators 11 is prevented. Correspondingly, the quality of the resulting optical coupling is assured, even in the case of large temperature fluctuations.

The segments 29 provided for accommodating the coupling elements 13 are preferably—such as shown in FIG. 2—embodied as flexible bellows. The thereby resulting, additional movability facilitates transport and assembly of the scintillation detectors of the invention.

The segment 33 provided on the free end of the protective tube 25 facing away from the photoelectric transducer 15 is preferably embodied as a closure cap, which seals an inner space of the protective tube 25.

The segment 27 provided on the end of the protective tube 25 facing the photoelectric transducer 15 is preferably terminally sealed by means of a light transmissive plug 39 installed in the segment. The end of the serially connected scintillator 11 facing the photoelectric transducer 15 rests against, especially is adhered to, the inner side of plug 39. Plug 39 is made of glass, for example.

The photoelectric transducer 15 is preferably arranged in a separate housing 41, which can be assembled mechanically with the protective tube 25 via a releasable mechanical connection. Moreover, also the measuring electronics 9 can be arranged in the housing 37. The optical connection of the transducer 15 to the series of scintillators 11 occurs preferably via a sealed, light transmissive plug 43, especially a glass plug, provided in a housing wall. To this end, the photoelectric transducer 15 can be applied in the housing 41 directly against the inner side of the plug 43. Provided on the housing 41 surrounding the plug 43 is a cylindrical connector 45, whose inner space is filled by a light conductor 47, such as e.g. a silicone disk.

Housing 41 and measuring tube 25 are preferably connected with one another in a mechanically releasable manner. For this, the centering sleeve 35 of the protective tube segment 27 at the housing 41 is screwed onto the connector 45 in such a manner that the plug 39 sealing the end of the segment 27 lies against the light conductor 47. For improving the optical coupling, a coupling paste is provided between plug 39 and light conductor 47.

Therewith, a totally modular construction of the scintillation detector is provided. Especially, housing 41 can be removed from the protective tube 25 and the therein located, serially arranged scintillators 11 without opening the internal spaces of housing 41 and protective tube 25. In this way, replacement, repair and/or maintenance of the photoelectric transducer 15 and of the measuring electronics 9 are/is performable, without negatively influencing the serially arranged scintillators 11. The scintillators 11 do not even have to be removed from the measuring location.

The invention claimed is:

1. A scintillation detector, especially one for a radiometric measuring device for measuring and/or monitoring a measured variable, especially one of: a fill level; or a density of a fill substance located in a container, comprising:
   two or more scintillators arranged in series relative to one another for converting thereon falling, radioactive radiation into light flashes, whose light propagates in said respective scintillator toward its ends;
   optical coupling elements arranged between said scintillators for establishing light transmitting connections between adjoining pairs of scintillators; and,
   connected at an end of the series, a photoelectric transducer, which converts light occurring in the series into an electrical signal corresponding to a radiation intensity striking said scintillators, wherein:
   at least one of said coupling elements is a mechanically flexible element, which includes a bundle of light conducting fibers, via which transmission of the light between said two scintillators connected with one another via said fibers occurs.

2. The scintillation detector as claimed in claim 1, wherein:
   said fibers are light conducting, scintillation fibers.

3. The scintillation detector as claimed in claim 1, wherein:
   said fibers are glass fibers or plastic light conductors.

4. The scintillation detector as claimed in claim 1, wherein:
   each of the two ends of said bundle is held in a collar, which is mechanically connectable via a centering sleeve with an end of said scintillator to be connected thereto.

5. The scintillation detector as claimed in claim 4, wherein:
   said fibers of said bundle are terminally planarly polished; and
   each of the polished ends of said bundle in the assembled state lies, with interpositioning of a coupling paste, against a planarly polished end face of a respectively adjoining scintillator.

6. The scintillation detector as claimed in claim 1, further comprising:
   a modularly constructed protective tube for accommodating the scintillators; and
   said protective tube is composed of segments, whose internal spaces are matched to the spatial dimensions of said scintillators and said coupling elements to be accommodated.

7. The scintillation detector as claimed in claim 6, wherein:
   segments provided for accommodating said flexible coupling elements are embodied as flexible bellows.

8. The scintillation detector as claimed in claim 1, wherein:
   said segment of said protective tube provided on the end facing away from said photoelectric transducer is embodied as a cap, which seals an inner space of said protective tube.

9. The scintillation detector as claimed in claim 1, wherein:
   said fibers of said coupling elements have a slight excess length, which is greater than or equal to a maximal, thermal expansion related, separation change between said scintillators connected with one another by said respective coupling element.

10. The scintillation detector as claimed in claim 1, wherein:
    said scintillators are arranged in an inner space of said protective tube, whose photoelectric transducer facing end is terminated by means of a light transmissive plug, especially a glass plug;
    said photoelectric transducer is arranged in a separate housing;
    said housing is connectable mechanically with said protective tube via a releasable mechanical connection; and
    said housing has a light transmissive plug, especially a glass plug, via which said photoelectric transducer is optically connectable to said series of scintillators.

* * * * *